United States Patent [19]
Shapland et al.

[11] Patent Number: 5,865,787
[45] Date of Patent: Feb. 2, 1999

[54] SIMULTANEOUS CARDIAC PACING AND LOCAL DRUG DELIVERY

[75] Inventors: James E. Shapland, Shoreview, Minn.; Keith R. Hildebrand, Houlton, Wis.

[73] Assignee: Cortrak Medical, Inc., St. Paul, Minn.

[21] Appl. No.: 710,146

[22] Filed: Sep. 13, 1996

Related U.S. Application Data

[60] Division of Ser. No. 177,175, Jan. 4, 1994, Pat. No. 5,634,899, which is a continuation-in-part of Ser. No. 110,109, Aug. 20, 1993, abandoned, which is a continuation-in-part of Ser. No. 957,209, Oct. 6, 1992, abandoned.

[51] Int. Cl.$^6$ ........................................................ A61N 1/30
[52] U.S. Cl. .................................. 604/21; 604/96; 607/120
[58] Field of Search .............................. 604/20–21, 96; 607/120

[56] References Cited

U.S. PATENT DOCUMENTS

| | | |
|---|---|---|
| 3,680,544 | 8/1972 | Shinnick et al. . |
| 4,146,029 | 3/1979 | Ellinwood, Jr. . |
| 4,301,794 | 11/1981 | Tapper . |
| 4,323,071 | 4/1982 | Simpson et al. . |
| 4,582,181 | 4/1986 | Samson . |
| 4,762,129 | 8/1988 | Bonzel . |
| 5,002,067 | 3/1991 | Berthelsen et al. . |
| 5,087,243 | 2/1992 | Avitall . |
| 5,236,413 | 8/1993 | Feiring . |
| 5,282,785 | 2/1994 | Shapland et al. . |
| 5,286,254 | 2/1994 | Shapland et al. . |
| 5,499,971 | 3/1996 | Shapland et al. . |
| 5,634,899 | 6/1997 | Shapland et al. . |

OTHER PUBLICATIONS

"Drug Pacemakers in the Treatment of Heart Block" by Judah Folman and David M. Long, Jr., *Annals of the New York Acedemy of Sciences*, V.III Art 1–3, 1963–64, pp. 857–868.

*Primary Examiner*—Mark Bockelman
*Attorney, Agent, or Firm*—Merchant, Gould, Smith, Edell, Welter & Schmidt, P.A.

[57] ABSTRACT

An apparatus and method for delivering a drug selectively and locally to internal body tissue with a catheter using electric current/voltage controlled in conjunction with active pacing of cardiac activity.

22 Claims, 4 Drawing Sheets

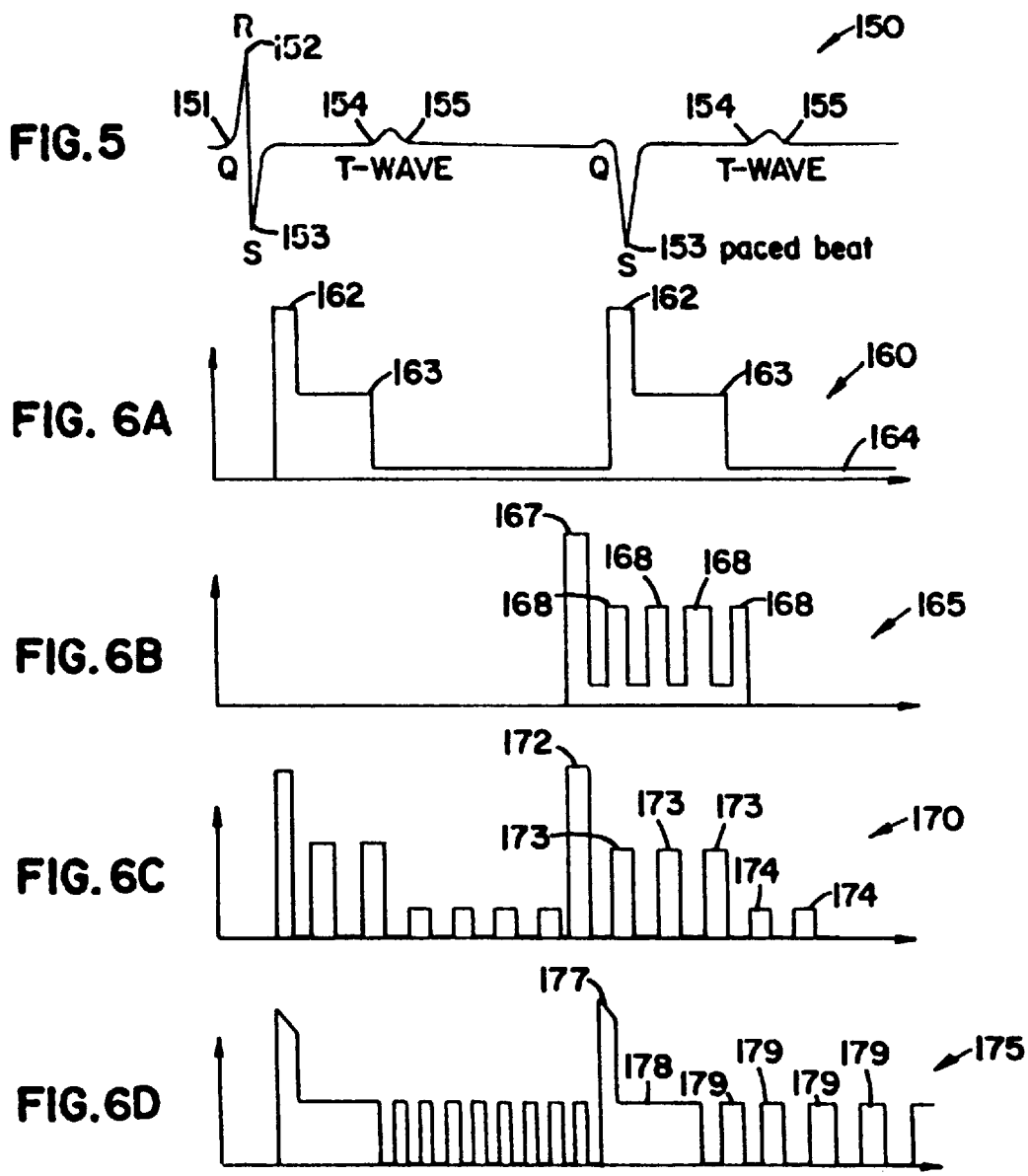

SIMULTANEOUS CARDIAC PACING AND LOCAL DRUG DELIVERY

This application is a divisional of 08/177,175 filed Jan. 4, 1994, now U.S. Pat. No. 5,634,899 which is a cip of 08/110,109, filed Aug. 20, 1993 now abandoned, which is a cip of 07/957,209 filed Oct. 6, 1992 now abandoned.

BACKGROUND OF THE INVENTION

1. Field of the Invention

The present invention relates generally to a drug delivery apparatus for selectively and locally delivering a drug to internal body tissue. More specifically, the present invention relates to an apparatus for providing electric current/voltage in conjunction with a catheter to selectively and locally deliver a drug to internal body tissue, wherein the electric current/voltage is controlled in synchronization with active pacing of cardiac electrical activity.

2. Description of the Related Art

Many techniques exist for delivering drugs or other medicaments to body tissue. These include, among others; oral administration; injection directly into body tissue such as through an intramuscular injection or the like; topical or transcutaneous administration where the drug is passively absorbed, or caused to pass, into or across the skin or other surface tissue; and intravenous administration which involves introducing a selected drug directly into the blood stream.

The advantages of localized internal drug delivery over systemic administration are known and described in, for example, commonly assigned U.S. patent application Ser. No. 07/937,464 filed Aug. 28, 1992 now U.S. Pat. No. 5,286,254, which is hereby incorporated by reference. That application also discusses some situations in which localized internal drug delivery is especially advantageous, including the treatment of a dilated vessel to reduce restenosis following PTCA (Percutaneous Transluminal Coronary Angioplasty) and the delivery of drugs to tumors.

U.S. patent application Ser. No. 07/937,464 filed Aug. 28,1992 now U.S. Pat. No. 5,286,254 also discusses the use of iontophoresis to enhance localized internal drug delivery. Problems are, however, associated with introducing an electrical current into the body, including muscle stimulation and contraction, as well as pain or other unwanted sensations. More importantly, the problem of cardiac arrhythmia (irregular rhythm) can easily arise when electrical current passes through the heart. The current source causing that problem can originate from an external source, within the heart itself, or adjacent to the heart—such as from a coronary artery.

Intensity (current density), frequency, waveform and duration of the electrical current used in iontophoresis have an effect on whether cardiac arrhythmias and other problems will occur, as well as the magnitude of those reactions. The threshold at which ventricular fibrillation occurs with various transthoracic and intracardiac electrical levels increases with higher frequency currents. The threshold of sensation also increases with higher frequencies.

One attempt to minimize the risk of iontophoresis-induced arrhythmias is disclosed in U.S. Pat. No. 5,087,243. An implanted myocardial iontophoresis patch system is disclosed there in which a pulsed current is supplied to the anodal patch. Electrical activity in the patient's heart is monitored and the iontophoresis current is pulsed on and off in synchronization with ventricular depolarization to avoid the interval during which the heart is vulnerable to electrically induced arrhythmias or unnatural heart rhythms.

This system suffers from the inherent inaccuracies of passive monitoring of cardiac electrical activity. Those inaccuracies can cause the delivery of iontophoretic electric current at the wrong time during a cardiac cycle which could cause cardiac arrhythmias.

Also, passive monitoring alone may not prevent arrhythmias if higher iontophoretic currents are used (e.g., greater than 1 $mA/cm^2$). Also, the disclosed preferred 80–100 msec pulses will not prevent vascular muscle stimulation resulting in vaso-constriction and may cause other unwanted stimulation or sensations.

Furthermore, the system described in U.S. Pat. No. 5,087,243 does not represent an optimized method for non-implantable iontophoretic drug delivery systems used near the heart. Non-implantable systems using catheters and other temporary devices preferably minimize the time of administration. An implantable system such as that described in U.S. Pat. No. 5,087,243 is, however, not optimized to minimize the time of administration as the system is always in place. By providing current for iontophoresis only during ventricular depolarization, the system of U.S. Pat. No. 5,087,243 cannot actively deliver any drug during a large percentage of the available time.

U.S. Pat. No. 5,236,413 to Feiring also discloses on/off pulsing of iontophoretic current in synchronization with passively monitored cardiac electrical activity to reduce the risk of inducing arrhythmias while enhancing drug delivery iontophoretically. As with the implantable system described above, however, the effectiveness of drug delivery is again limited by the relatively high proportion of time during which iontophoretic current is not provided.

Another disadvantage of the Feiring device and method is reliance on passive monitoring of cardiac electrical activity to minimize the risk of arrhythmias. Passive monitoring is not always accurate and the chance exists for errors which could result in cardiac arrhythmias.

Accordingly, there is a need in the art for an apparatus for delivering a drug selectively and locally to internal body tissue with a catheter using electric current/voltage controlled in conjunction with active pacing of cardiac electric activity.

SUMMARY OF THE INVENTION

In accordance with the present invention, an apparatus and method are provided for delivering a drug selectively and locally to internal body tissue with a catheter using electric current/voltage controlled in conjunction with active pacing of cardiac electric activity.

More specifically, the invention involves an apparatus and method for delivering a drug or combination of drugs substantially transversely to a body passageway, such as a blood vessel or esophagus, to treat a localized region of the passageway itself and/or tissue located adjacent to the passageway using electric current/voltage while simultaneously pacing the patient's heart to reduce the risk of arrhythmia. Also contemplated is delivery of a drug or combination of drugs directly to internal body tissue using the apparatus of the present invention outside of a body passageway.

In one preferred embodiment, the apparatus includes a flexible member adapted for insertion into the body passageway or tissue and a drug delivery means connected with the flexible member for delivering the drug to or through a local area of the passageway wall or tissue. The drug delivery means could include a drug delivery chamber for receiving a selected drug in fluid form, a polymer matrix material containing a drug, or a combination of the above. The chamber can be defined in part by a permeable membrane to control transport of a drug therethrough, i.e. constructed of at least perforated, permeable, microporous or semipermeable material through which the drug is intended to pass, that is, selectively permeable.

The preferred apparatus according to the present invention includes drug delivery current/voltage means to provide electric current/voltage to transport drugs or other medicaments from the drug delivery means and into the tissue surrounding the apparatus.

The preferred apparatus according to the present invention also includes pacing means to actively pace the patient's heart to ensure that the drug delivery current/voltage is provided at the proper levels and at the desired times to further reduce the risk of arrhythmias. Active control over heart activity and the drug delivery current/voltage allows the safe delivery of higher current/voltage levels which, in turn, further enhances the drug delivery process.

One preferred apparatus according to the present invention also provides pulsed drug delivery current/voltage to further maximize drug delivery while minimizing the negative side effects associated with direct current. Those side effects include cardiac arrhythmias, muscle stimulation or other unwanted side effects.

When combined with actively pacing cardiac electrical activity, localized internal drug delivery enhanced by electric current/voltage can be safely and effectively maximized. Although passive monitoring of heart activity can be performed, it is typically less reliable than active control and, therefore, increases the risks of induced cardiac arrhythmias.

One preferred embodiment of an apparatus according to the present invention incorporates drug delivery electrodes and pacing electrodes in a bipolar configuration. One advantage of a bipolar electrode configuration is a localization of the drug delivery current/voltage to the region adjacent the drug delivery site, thereby further reducing the potential for cardiac arrhythmias throughout the entire heart.

These and other advantages and features of the present invention will become apparent with reference to the drawings, the description of the preferred embodiment and method and the appended claims.

DESCRIPTION OF THE DRAWINGS

FIG. 5 depicts an electrocardiogram of the activity in a heart.

FIGS. 6A–6D depict embodiments of waveforms for use according to the invention.

DETAILED DESCRIPTION OF PREFERRED EMBODIMENTS AND METHODS

Figure 1:
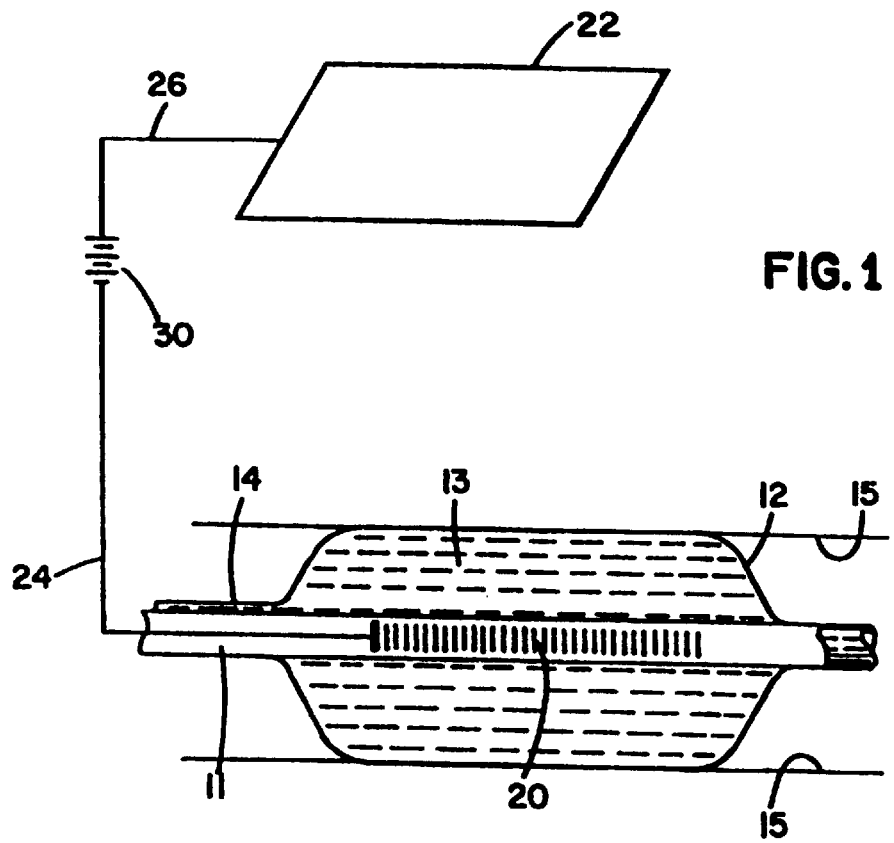
FIG. 1 is a partial view in partial cross-section of one drug delivery apparatus according to the present invention positioned in a blood vessel.
Figure 2:
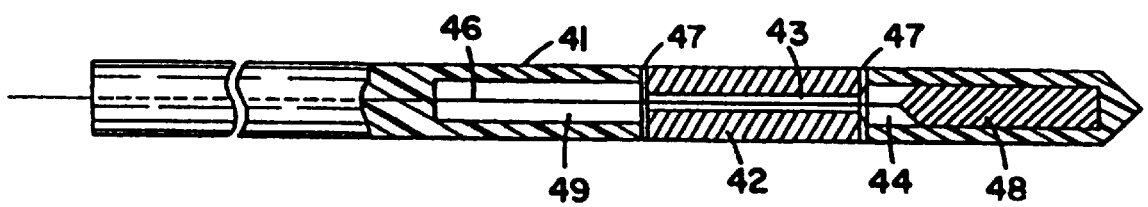
FIG. 2 is a partial view in partial cross-section of an alternate embodiment of a drug delivery apparatus according to the present invention.
Figure 3:
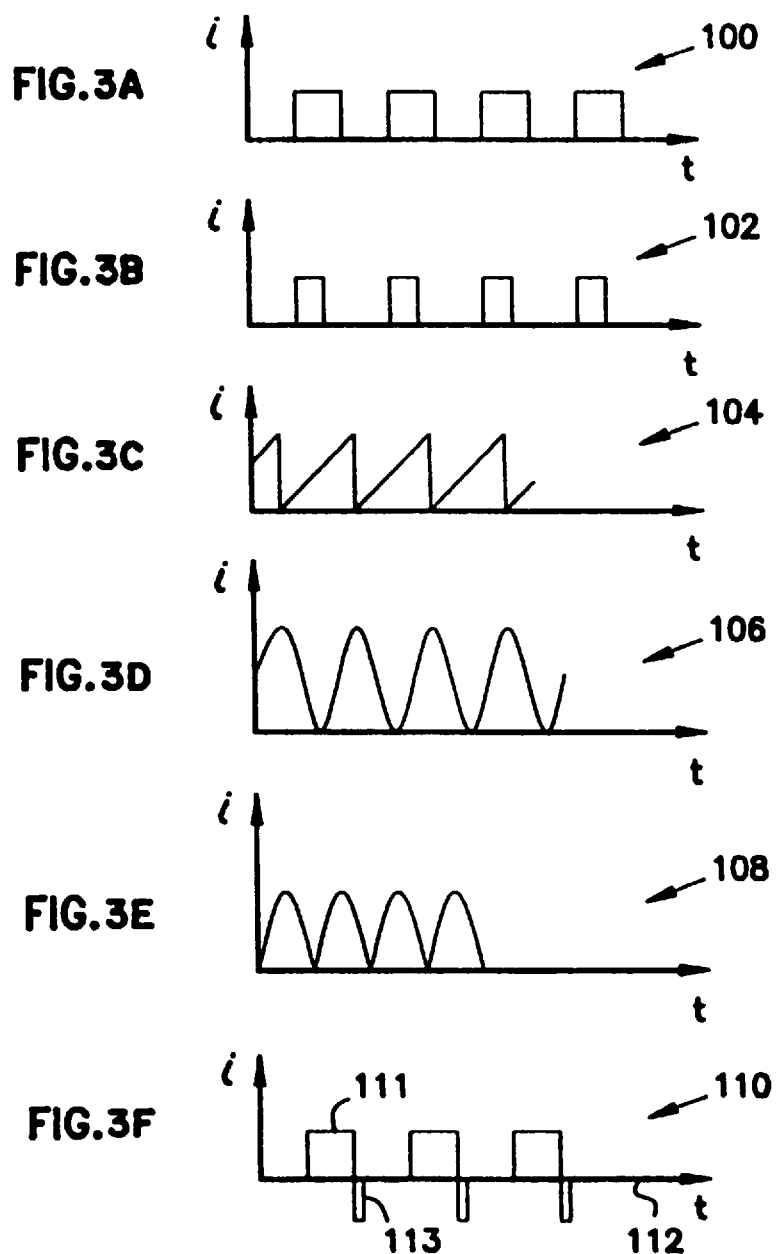
FIGS. 3A–3F depict a variety electric waveforms for use with catheters according to the present invention.

FIGS. 1 and 2 illustrates two preferred embodiments of drug delivery apparatus in accordance with the present invention. In general, the apparatus provides a means and a system for delivering a drug or combination of drugs to, or through, a localized area of a passageway or a localized area of tissue outside of a passageway. As a result, the present invention provides the ability to treat the localized area of the passageway and/or tissue with minimal, if any, undesirable effect on other body tissue.

The drug delivery apparatus typically comprises a catheter modified to provide local internal drug delivery in conjunction with electric current/voltage. The term "catheter" as used in the present application is intended to broadly include any medical device designed for insertion into a body passageway to permit injection or withdrawal of fluids, to keep a passage open or for any other purpose. It is contemplated that the drug delivery apparatus of the present invention has applicability for use with any body passageways including, among others, blood vessels, the esophagus and the like.

Catheters are commonly used in percutaneous transluminal coronary angioplasty (PTCA) procedures to dilate stenosed blood vessels or arteries. These catheters may be modified according to the present invention. They include, but are not limited to, over the wire catheters of the type illustrated generally in U.S. Pat. No. 4,323,071; fixed wire catheters of the type illustrated in U.S. Pat. No. 4,582,181; and rapid exchange catheters as illustrated in U.S. Pat. No. 4,762,129. The disclosure of each of the above patents is incorporated herein by reference for their teachings relating to catheter construction.

As used in the present application the term "drug" is intended to broadly include any medicament or other substance which is desired to be delivered to body tissue for therapeutic, diagnostic or any other purpose. The term "catheter" is intended to broadly include any medical device designed for insertion into internal body tissue or a body passageway to permit injection or withdrawal of fluids, to keep a passage open, or for any other purpose. It is contemplated that the drug delivery apparatus of the present invention is applicable for use with any body passageways including, among others, blood vessels, the esophagus and the like.

All apparatus according to the present invention rely, at least in part, on iontophoresis or its counterpart, electroporation, to enhance delivery of the drugs into tissue surrounding the distal ends of the catheters. Iontophoresis technology uses an electrical potential or current across a permeable barrier to drive ionic drugs or drag nonionic drugs in an ionic solution. Iontophoresis can facilitate both transport of a drug across a permeable membrane and enhance tissue penetration. Electroporation employs high voltage pulses, relative to the voltage levels associated with iontophoresis, to transport drugs similar to iontophoresis, and can also provide for poration of cells to enhance cellular uptake of drugs. The application of electroporation in localized internal drug delivery apparatus is described in U.S. patent application Ser. No. 08/129,252, filed on Sep. 29, 1993 now abandoned, which is hereby incorporated by reference.

For the purposes of the present application, iontophoresis and/or electroporation are interchangeable, i.e., it is advantageous to provide for active pacing of cardiac activity in conjunction with either iontophoresis or electroporation.

In the application of iontophoresis or electroporation, two electrodes, one on each side of the barrier, are utilized to develop the required potential or current flow. In particular, one electrode may be located inside of the catheter in opposed relation to the drug delivery wall of the catheter while the other electrode may be located at a remote site on a patient's skin. Alternate embodiments may include both electrodes on the catheter body, with one electrode inside the drug delivery/balloon chamber and the opposing electrode located along the catheter body (See FIG. 4 which is described more fully below).

FIG. 1 illustrates one preferred embodiment of a drug delivery apparatus according to the present invention. The balloon 12 is shown in its inflated state within an arterial vessel in which the vessel walls are indicated by the reference numeral 15. During intravessel procedures, such as PTCA, a guide wire (not shown) is first inserted into the selected artery to a point past the stenotic lesion. The dilatation catheter including the catheter body 11 and balloon 12 is then advanced along the guide wire to the desired position in the arterial system in which the balloon portion 12 traverses or crosses the stenotic lesion.

The balloon 12 is then inflated by introducing an inflation fluid through the balloon lumen 14 into the interior chamber 13 of the balloon 12. During inflation, the outer surfaces of the balloon 12 press outwardly against the inner surfaces of the vessel wall 15 to expand or dilate the vessel in the area of the stenotic lesion. Alternately, the balloon 12 may be expanded only to provide intimate contact between the balloon wall and the vessel wall 15 or other tissue located thereon. In accordance with the present invention, and, in particular, in accordance with the embodiment of FIG. 1, the balloon 12 is inflated by introducing a drug solution through the balloon lumen 14 and into the interior of the balloon portion 12.

The structure of the catheter body 11 and the balloon lumen 14 is similar to conventional catheter design which is known in the art and an example of which is shown in U.S. Pat. No. 4,323,071. The balloon 12 of FIG. 1, however, is distinguishable from conventional catheter balloons in that the balloon 12 is constructed from a material which permits the transport or passage of a drug or fixative across the balloon surface.

The catheter electrode 20 is located on or within the catheter body 11 while the remote electrode 22, the body surface electrode, is located on the body surface or within the body of the patient. The remote electrode 22 will typically consist of an external patch electrode, although internal electrodes positioned remote from the internal electrode 20 are also contemplated. The remote internal electrode may be attached near the proximal end of the catheter body 11 or may be unattached to the catheter body 11.

In the embodiment illustrated in FIG. 1, a coil electrode 20 is provided around the body 11 of the catheter. The preferred electrode materials should minimize undesired oxidative/reductive reactions or production of competitive ions during the electroporation and/or iontophoresis. Preferred electrode materials are silver for anodal electrodes and silver chloride plated silver for cathodal electrodes. Other potential electrode materials include platinum or carbon, although it will be understood that many other materials could be substituted provided that they are biocompatible and capable of handling the voltage levels to which they well be exposed.

Furthermore, the electrode 20 could also be provided in many other geometric forms, such as a hollow cylinder, a sphere with a hole formed through the sphere, etc. One consideration in choosing the shape of the electrodes is to confine current to target zone so that the myocardium is not affected. Electrode shapes can also help to control current density, particularly if electroporation is used in conjunction with active cardiac pacing.

Electric current/voltage for both the iontophoresis/electroporation and pacing processes is produced between the electrodes 20 and 22 by an external power source 30 through the electrical leads 24 and 26, respectively.

It will be understood that the drug desired to be delivered will preferably have an ionic charge which allows it to be moved by electric current (i.e., by causing the molecules to move towards the pole of opposite charge from that of the molecules sought to be moved).

Alternatively, however, the drug can consist of essentially neutral, non-polar molecules, but may still be delivered by an electric field using iontohydrokinesis. Iontohydrokinesis involves the movement of polar water molecules in an electric field. The drug molecules in solution in the water move with the polar water molecules to deliver the drug to the targeted internal body tissue. As used herein, the term "iontophoresis" is also meant to broadly include iontophoresis, iontohydrokinesis and similar effects.

During operation of the device of FIG. 1, the balloon 12 is first positioned across the stenotic lesion in the manner described above. The balloon interior 13 is then inflated with the drug through the lumen 14. After inflation, power supply/pacing circuit 30 is activated. The pacing portion of the apparatus would initially sense intrinsic cardiac electrical activity to ensure that the initial pacing pulse is not delivered during the vulnerable period of the intrinsic heart rhythm. This portion of the circuit is similar to the inhibitory pacing circuits used in conventional implantable and external pace-makers.

At the appropriate coupling interval, the pacing circuit would activate and emit a pacing pulse to stimulate the heart. In the device of FIG. 1, the internal electrode, i.e., electrode 20, would be used in combination with the remote electrode 22 to provide the pacing pulse. The energy of the initial pacing pulse should be of sufficient amplitude and duration to ensure capture or stimulation of the heart. Typically, pulse duration would be in the range of 0.5 to 5 milliseconds.

Immediately after the pacing pulse has been delivered, the power supply 30 would provide a preferred drug delivery current/voltage to transport the drug across the balloon wall 12. After a specified duration corresponding to the refractory period of the heart, the drug delivery current/voltage could be reduced to a predetermined level to allow the heart muscle to repolarize. The drug delivery current/voltage could then continue at the predetermined level (or, it will be understood, the current could be turned off) until the next pacing pulse was delivered to again start the cycle.

The apparatus of FIG. 1 can utilize both pressure and electric current/voltage as the driving force, although, it is contemplated that electric current/voltage could be utilized alone. It is also contemplated that electric current/voltage by itself, or in combination with a solvent like DMSO as a carrier, could yield drug transport into or through a vessel wall at pressures less than about 20 mm Hg above normal ambient vessel wall pressure and preferably at less than about 5 mm Hg, thereby avoiding substantial damage to the vessel wall known to occur at higher pressures.

Additionally, the polarity of the electrodes may be reversed to recapture excess drug delivered to or through the vessel wall.

Alternatively, the catheter of FIG. 1 may be used after dilation has already been effected by another catheter earlier used to dilate the vessel. In this case, the drug delivery catheter is preferably expandable only to bring the balloon 12 into intimate contact with the vessel wall for drug delivery.

In the preferred embodiment, it is contemplated that the material from which the balloon 12 of FIG. 1 is constructed will be a microporous membrane material such as dialysis membrane. It is contemplated, however, that various other permeable or semipermeable materials may also be used including, without limitation, cellulose, cellulose acetate, polyvinyl chloride, polysulfone, polyacrylonitrile, silicon, polyurethanes, natural and synthetic elastomers. Examples of suitable microporous membranes are polyester, polyolefin, a fluorpolymer, or the like having pore sizes smaller than 3 microns and preferably from about 10 Å to 3 microns, and even more preferably from about 50 Å to about 0.1 microns. Membranes with pore sizes in the most preferred range will be provided with a pore density in the range from about $10^4$ to about $10^{11}$ pores/cm$^2$, or more.

It is contemplated that the particular material from which the balloon 12 is constructed will depend to some extent on the specific composition of the drug to be delivered as well as the driving pressures which may be developed within the balloon chamber 13. In the structure of FIG. 1, the preferred material from which the balloon 12 is constructed is inelastic and the pressure generated within the balloon chamber 13 to aid in transport of the drug solution across the balloon walls is between about 1 and about 90 psi.

Other features and constructions of alternate catheters which provide drug delivery through permeable membranes along with electrodes suitable for drug delivery/pacing are described in commonly-assigned U.S. patent application Ser. No. 07/705,731 filed on May 24, 1991 now abandoned; Ser. No. 07/937,464 filed on Aug. 28, 1992 now U.S. Pat. No. 5,286,254; and 07/956,789 filed on Oct. 5, 1992 now U.S. Pat. No. 5,282,785—all of which are hereby incorporated by reference.

Commonly-assigned U.S. patent application Ser. No. 08/123,374 filed on Sep. 17, 1993 now U.S. Pat. No. 5,458,568 is also incorporated by reference for its disclosures relating to catheters including drug delivery electrodes in combination with selectively permeable membranes and methods for using the same to deliver drugs internally.

Additionally, commonly-assigned U.S. patent application Ser. No. 08/129,252 now abandoned filed on Sep. 29, 1993 describes catheters and methods of performing localized internal drug delivery using electroporation to enhance the drug delivery. That application is also hereby incorporated by reference for its disclosure relating to the construction of catheters and methods of electroporation to enhance localized internal drug delivery.

FIG. 2 illustrates the distal end of an alternate embodiment of a catheter according to the present. The catheter includes an elongated, flexible catheter body 41, a drug delivery means in the form of a drug-impregnated polymer matrix 42 positioned in the catheter body 41 near its distal end.

In the embodiment illustrated in FIG. 2, impermeable end caps 47 are located on either end of the substantially cylindrical polymer matrix 42 to prevent movement of the drug in the matrix 42 longitudinally along the catheter body 41. The end caps 47 are, however, optional and may be added or removed as desired depending on the extent of leakage in the axial direction during drug transport and any undesirable effects that the leakage may have on the patient.

An electrode passageway 44 extends along the catheter body 41 on either side of the polymer matrix 42. A wire 46 is attached to the electrode 48 which is positioned in the distal end of passageway 44. The wire 46 extends from the proximal end of the catheter body 41 to its distal end where it is attached to electrode 48.

The embodiment depicted in FIG. 2 is designed to expand radially when electrode 48 is pulled into position within the polymer matrix 42. After the electrode 48 is in position, the power supply/pacing apparatus can be activated to provide a suitable drug delivery current/voltage along with pulses for cardiac pacing.

Because the device in FIG. 2 is to be expanded, the polymer matrix material 42 used as the drug reservoir should be compliant and expandable and, ideally, non-compressible or minimally compressible. The material must be compliant and expandable to allow sufficient expansion of the polymer matrix material 42 by the expansion means, which comprises an electrode 48 as depicted in FIG. 2. Alternate expansion means can include wire baskets or balloons.

The compressibility of the polymer matrix material 42 is preferably limited to maximize the diameter of the catheter when the polymer matrix material 42 is expanded, thus ensuring intimate contact between the polymer matrix material 42 and target tissue to enhance drug transfer or to dilate a vessel in which the catheter is located. It is also contemplated that the polymer matrix material 42 could be compressible, provided that the expansion means is designed to ensure intimate contact in spite of the compressibility of the polymer matrix material.

In the embodiments which do not expand radially, in which case the electrode 48 would be provided within the polymer matrix material 42, it will be understood that the polymer matrix material 42 need not be expandable or non-compressible and may, in fact, be rigid if desired.

As used in conjunction with the present invention, the term "polymer matrix" includes synthetic polymers in the form of hydrogels or other porous or drug-permeable configurations or morphologies, such as polyvinyl alcohol, polyvinylpyrrolidone and polyacrylamide, polyethylene oxide, poly(2-hydroxy ethyl methacrylate); natural polymers such as gums and starches; synthetic elastomers such as silicone rubber, polyurethane rubber; and natural rubbers. The above examples are provided for reference only, and the range of suitable polymer matrix materials should not be construed as limited to those materials listed above.

The polymer matrix material can also be hydrophilic or hydrophobic, provided it meets the physical characteristics described above.

Drugs may be incorporated into the polymer matrix material by a variety of methods. The drug can be incorporated into the material as the polymer solution or dispersion is formed into the preferred annular shape; it can be added to the polymer matrix material after formation into the desired shape either passively or actively (through, for example, such methods as iontophoresis or electroporation); the drug can be dissolved in a solvent (e.g., water, propylene, glycol, etc.) and the resulting solution can be incorporated into the polymer matrix material; or the drug molecules can be incorporated directly into the polymer matrix material.

Other features and constructions of alternate catheters incorporating drugs loaded into a polymer matrix material along with electrodes and a discussion of methods of delivering drugs with the same which are suitable for drug delivery/pacing are described in commonly-assigned U.S. patent application Ser. No. 07/973,263 filed Nov. 9,1992, now abandoned—which is hereby incorporated by reference.

The various catheters described above with respect to FIGS. 1 and 2, as well as in the applications incorporated by reference, are all preferably adapted to use electric current/voltage as a driving force to transport a drug to internal body tissue. Direct current is theorized to be most effective for iontophoresis, although, as discussed above, direct current in the absence of active pacing may cause cardiac arrhythmias, vascular spasms, muscle stimulation and other undesirable side effects.

Because of the problems associated with the use of direct current, the preferred methods of drug delivery using electric current/voltage involve pulsed waveforms. More preferably, those waveforms provide a net flow of current to or from the catheter electrodes. Possible waveforms contemplated for use in the invention are depicted in FIGS. 3A–3F and include square waves 100, rectangular waves 102, sawtoothed waves 104, sinusoidal waves that do not reverse polarity 106, rectified sinusoidal waves 108, and modified rectangular waves 110 (or other waveform shapes as desired) which do reverse polarity but provide a net flow of current in a desired direction.

The common characteristic of the most preferred waveforms is that they all provide net flow of current from the catheter electrode. The majority of the preferred waveforms never reverse polarity, while others can reverse polarity briefly to provide better control over the inducement of cardiac arrhythmias. Even in those waveforms which do reverse polarity, however, there is preferably a net flow of current in one direction as depicted by waveform 110 in FIG. 3F. Current flow in a first direction is indicated by area 111 above line 112 and current flow in a second (opposite) direction is indicated by area 113 below line 112. As a result, summing the areas 111 and 113 shows a net positive flow of current in the first direction as area 111 is larger than area 113.

Although the most preferred waveforms are pulsed and provide a net flow of current in one direction, it is also within the scope of the present invention to employ direct current in conjunction with cardiac pacing, as well as waveforms which offer no net flow of current (such as sinusoidal waveforms).

The frequency and maximum intensity of any waveforms used in the present invention can be varied to provide the maximum transfer rate while avoiding potential problems caused by the electrical current.

The preferred frequency range for iontophoresis begins at about 200 Hz and increases to a maximum of about 10 MHz, with the most preferred range lying between 2–15 kHz. It will be understood that the frequency can be varied within these ranges to maximize the rate of iontophoretic transfer for a given drug used in the catheters of the present invention.

Methods of providing a variety of pulsed iontophoretic waveforms are discussed in copending and commonly assigned U.S. patent application Ser. No. 08/110,109, filed on Aug. 20, 1993 now abandoned and Ser. No. 07/957,209 filed on Oct. 6, 1992 now abandoned, both of which are hereby incorporated by reference.

Regarding electroporation, the frequency at which pulses are provided can vary depending on the desired treatment and area of the body being treated. Typically, however, pulse frequency will be based largely on the patient's heart rate. Pulses are preferably delivered at only those portions of time when the patient's heart is least susceptible to induced arrhythmias, i.e., during the refractory period. As a result, pulse frequency will typically lie within the range of about 0.017 to about 10 Hz, more preferably within the range from about 0.1 to about 5 Hz, and most preferably within the range from about 1 to about 2 Hz. Furthermore, it is envisioned that a multiple number of pulses can be delivered at the above frequencies only during the refractory period and that no pulses will be delivered at other times.

The initial voltages useful in conjunction with electroporation can range from 100–10,000 volts or more. The electrodes used to provide the voltage are typically spaced approximately 0.5–5.0 cm apart in bipolar electrode configurations and approximately 5.0–10.0 cm or more apart in unipolar electrode configurations. The result is that electric field strengths can range from a low of about 10 V/cm to a high of about 20,000 V/cm or more. Preferred field strength ranges lie between about 100 to about 10,000 V/cm, more preferably from about 500 to about 8000 V/cm, and most preferably from about 1000 to about 5000 V/cm.

Pulse duration also plays a role in electroporation. As envisioned, pulse duration will range from about 1 $\mu$sec to about 1 second, more preferably from about 1 $\mu$sec to about 350 msec and most preferably from about 1 $\mu$sec to about 100 msec.

Where a radio frequency (rf) source is used to provide a high frequency pulse train for electroporation, the pulse duration can consist of a train of shorter pulses which deliver the desired level of electric current over the desired pulse duration period. Within such a pulse train, the frequency of the pulses preferably lie within the range from about 200 Hz to about 100 kHz, with a more preferred range lying between about 5 to about 15 kHz.

To the extent that it controls the amount of electrical energy available, capacitance also plays a role in the effect of electroporation on diffusion and/or poration. This is true, of course, only in those systems which rely on capacitive discharge to provide the electrical energy source. It is envisioned that the range of capacitive charge available will extend from approximately 0.01 $\mu$f to an upper limit of approximately 2770 $\mu$f.

Additional details regarding the application of electroporation can be found in U.S. patent application Ser. No. 08/129,252 filed on Sep. 29, 1993 now abandoned, which is incorporated by reference above.

For use with the present invention, two or more dedicated pacing electrodes could be provided on the catheter body itself and used for pacing cardiac electrical activity in a bipolar method. Alternatively, one additional pacing electrode could be provided proximate the distal end of the catheter and electrode 22 (used to provide electrical current for drug delivery in the apparatus of FIG. 1) could be paired to provide pacing of the cardiac activity as well as drug delivery current/voltage, also in a bipolar method.

The terms "bipolar" and "unipolar" pacing are commonly known in the art of heart pacing. Briefly, however, bipolar pacing refers to pacing performed using electrodes which are located in relatively close proximity to each other. Unipolar pacing is performed using electrodes which are located relatively far apart. Unipolar pacing, as used in conjunction with the present invention, can include using one electrode within the patient and another electrode located on the patient's skin or within the patient's body, but at a location too removed from the other electrode within the patient to be considered a bipolar electrode configuration.

Unipolar pacing and drug delivery could also be accomplished through a number of electrode combinations. The simplest combination would be, referring to FIG. 1, to use the same electrodes 20 and 22 which provide electrical energy for drug delivery to pace cardiac electrical activity. Alternatively, an additional (dedicated) pacing electrode could be provided proximate the distal end of the catheter and electrode 22 could be paired with the additional pacing electrode to provide pacing of the patient's heart activity, also in a unipolar method.

Figure 4:
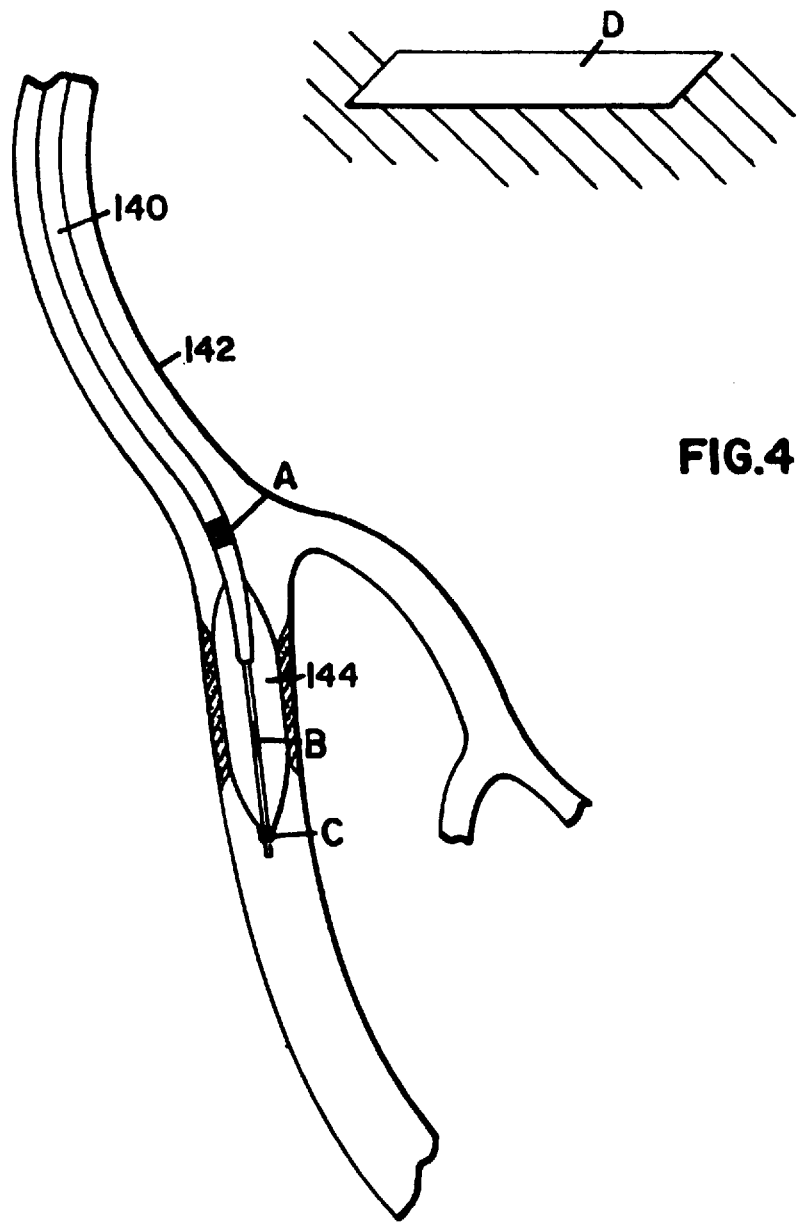
FIG. 4 is a schematic diagram of various electrode configurations on, around and within a drug delivery apparatus for use with the methods and apparatus according to the present invention.

The same catheter electrode configurations used for unipolar or bipolar pacing of heart electrical activity could be used for the drug delivery current/voltage as well. Referring to FIG. 4, which illustrates the different electrode configurations for a catheter 140 located within a vessel 142, unipolar drug delivery/pacing could be accomplished by using electrode B located in the drug delivery chamber 144 and a second electrode D located on the surface of the patient. Alternately, electrode B could be paired with an electrode (not shown) located remotely on the catheter body 140 or at any other remote location not on the catheter body 140, such as, for example, a subcutaneous electrode.

Also referring to FIG. 4, bipolar drug delivery/pacing could be accomplished using electrode B located in the drug delivery chamber 144 paired with either or both of electrodes A or C located on the catheter body 140 proximate the drug delivery chamber 144. It will also be understood that any electrodes paired with electrode B may not necessarily be located on the catheter body 140, but may, instead, simply be located proximate the drug delivery chamber 144. For all practical purposes, however, electrodes paired with electrode B will typically be provided on the catheter body 140 for simplicity.

The bipolar electrode configurations described herein localize the drug delivery current/voltage to the region adjacent the drug delivery site, thereby further reducing the potential for cardiac arrhythmias throughout the entire heart.

FIG. 5 depicts an electrocardiogram waveform 150 indicating electrical activity during beating of a heart. The various phases of a normal, unpaced heartbeat are depicted in the first half of waveform 150, including ventricular depolarization from point 151 to 152 and the refractory period which begins at point 152 and ends at the start of the repolarization period indicated by point 154.

The heart is most susceptible to arrhythmias stimulated by external electrical stimuli during the repolarization (or vulnerable) phase which begins with the T-wave period running from points 154 to 155.

Typical electric drug delivery systems use a single peak current level during all portions of the cycle which is below the stimulation threshold determined during the repolarization period to avoid unwanted arrhythmias.

The present invention, however, paces the patient's heart and varies the electric drug delivery current/voltage to ensure that the proper amount of current/voltage is delivered at the proper times. As a result, the present invention is able to vary the peak current level based on the changing threshold to enhance drug delivery during all phases of the cardiac cycle, in addition to preferably providing the electrical energy in a high frequency pulsed waveform to further reduce the chance of unwanted arrhythmias.

The waveforms depicted in FIGS. 6A–6D are placed directly below the waveform 150 of FIG. 5 to show the synchronization of waveforms 160, 165, 170 and 175 with waveform 150. The depicted waveforms are in no way meant to limit the scope of the present invention, and it will be understood that any waveforms falling within the scope of the invention as claimed will form a part of the present invention.

Waveform 160 in FIG. 6A depicts the use of direct current for iontophoresis only in combination with pacing according to the present invention. Intrinsic cardiac activity is monitored to begin pacing. The initial pacing pulse 162 is optional. As shown in the second half of FIG. 5, the second pacing pulse 162 aborts the Q–R segment of the ECG as the pacing equipment is used to provide the necessary electric current. After each of the pacing pulses 162 or a sensed beat (if no initial pacing pulse 162 is provided), a predetermined level of direct current 163 is provided to perform the iontophoretic drug delivery. That level of current is further reduced to level 164 during the repolarization period beginning at approximately point 154 in the ECG. It will be understood that waveform 160 will be repeated for as long as necessary to accomplish the desired drug delivery.

It will be understood that pacing pulse 162 could alternately be provided at a current/voltage level below that used for the iontophoresis current.

The period between pacing pulses 162 is preferably less than the period between intrinsic beats to prevent pacing directly into an intrinsic beat. That method is known in pacing as the escape interval. If an intrinsic beat is sensed before the next pacing pulse 162, the timing circuit resets the escape interval and restarts the pacing process. In that way, the cardiac activity can be "captured" by the pacing equipment.

FIGS. 6B–6D depict alternate versions utilizing some preferred pulsed currents. Typically, the relative current/voltage levels depicted are similar to what may be used in an iontophoresis-based system incorporating active cardiac pacing according to the present invention. It will, however, be understood that the relative current/voltage values would differ for electroporation-based systems, along the lines of the voltage levels described above.

Waveform 165 as depicted in FIG. 6B includes a acing pulse 167 followed by pulses 168. In this waveform, the current level is reduced to 0 at the start of the vulnerable period, i.e., the repolarization period. Waveform 165 differs from that depicted in FIG. 6A in that the initial pacing pulse 167 is timed to occur a set interval after the last sensed intrinsic beat. That interval is the "escape interval" described above. Alternately, of course, an initial pacing pulse could be provided as is provided in waveform 160 of FIG. 6A.

Also in waveform 165, pulsed current is preferably applied because the peak current level is typically greater for pulsed current than that allowed when only direct current is provided. As a result, drug delivery can be enhanced when pulsed iontophoresis current is provided.

Waveform 170 is yet another alternate waveform which includes a pacing pulse 172 followed by pulses 173 at one level and further followed by pulses 174 which are limited to a predetermined threshold below the level of pulses 173 during the repolarization period to further reduce the risk of arrhythmia.

Pulsed current is preferably also applied during the refractory period in waveform 170 to enhance during delivery by providing some current/voltage at all times during the heart cycle. Although pulsed current is the preferred version, it will, however, be understood that direct current which is varied according to cardiac activity can be used in conjunction with pacing to perform the drug delivery as depicted with waveform 160 in FIG. 6A.

Waveform 175 in FIG. 6D depicts yet another alternate embodiment of a waveform useful according to the present invention. As shown there, the waveform 175 includes a truncated capacitive pacing pulse 177 followed by a direct current portion 178 which terminates at the beginning of the repolarization period and converts to pulses 179 during the repolarization period to further reduce the risk of arrhythmia.

It will be noted that the frequency of the pulses in the waveforms described above can be varied between the refractory period and the remaining portions of the cycle, although a constant frequency during all portions of the cycle is also contemplated.

Furthermore, although waveforms 160, 165, 170 and 175 are depicted as rectangular (supplied by a chopped DC current supply), the waveforms could also have many other shapes such as square waves, saw-toothed waves, sinusoidal waves that do not reverse polarity, rectified sinusoidal waves, and modified rectangular waves (or other waveform shapes as desired) which may reverse polarity but provide a net flow of current in a desired direction (for iontophoresis-based systems). Examples of such waveforms are described in commonly assigned U.S. patent application Ser. No. 08/110,109, filed on Aug. 20, 1993 now abandoned and Ser. No. 07/957,209 filed on Oct. 6, 1992 now abandoned, both of which are incorporated by reference above.

To provide the waveforms depicted in FIGS. 6A–6D, the present invention preferably utilizes known pacing equipment and circuits as well as known circuits useful for iontophoresis/electroporation. Alternatively, it will be understood that any circuit used to deliver the drug delivery current/voltage could also be modified to deliver the pacing pulses as well in an integrated circuit.

Although the description of the preferred embodiments and methods has been specific, it is contemplated that various modifications could be made without deviating from the spirit of the present invention. For example, drugs may be delivered to the walls of an artery, perhaps already dilated, through a catheter balloon wall which is perforated. An antitumor drug may be similarly delivered through a perforated balloon wall for delivery through a vessel wall to an adjacent tumor. Such perforated balloons are combined with iontophoresis or electroporation to drive the drug into or through the vessel wall. Further, a drug can be delivered to an internal body tissue through a selectively permeable membrane portion of a drug delivery component connected to a catheter. When the catheter and connected drug delivery component are directed to a body tissue target area over a rigid probe or trocar the amount of drug delivered to the tissue to be treated is maximized and the leakage of drug back along the catheter and away from the target area is minimized. Also, many different waveforms other than those specifically mentioned could be used. Accordingly, it is intended that the scope of the present invention be dictated by the appended claims, rather than by the description of the preferred embodiment and method.

We claim:

1. An apparatus for local delivery of a drug to internal body tissue of a patient comprising:
   (a) a catheter having drug delivery means;
   (b) a plurality of electrodes, at least one of said electrodes being operably connected to the catheter;
   (c) drug delivery current/voltage means electrically connected to at least two of said electrodes for transport of said drug from said drug delivery means to said internal body tissue; and
   (d) pacing means electrically connected to at least two of said electrodes, the pacing means being configured to generate a pulse for stimulating the patient's heart to begin the refractory period of the heart beat, the drug-delivery current/voltage means being synchronized with the pacing means to transport at least a portion of said drug after generation of said pulse.

2. The apparatus of claim 1, wherein said at least two electrodes electrically connected to said drug delivery current/voltage means are also said at least two electrodes electrically connected to said pacing means.

3. The apparatus of claim 1, wherein said drug delivery current/voltage means and said pacing means are provided as a single apparatus for both iontophoretic transport and controlling cardiac activity.

4. The apparatus of claim 1, wherein said drug delivery means comprises:
   (1) a drug delivery chamber proximate said distal end of said catheter;
   (2) a permeable membrane defining at least a portion of said drug delivery chamber; and
   (3) a fluid delivery lumen extending between said proximal end of said catheter and said drug delivery chamber.

5. The apparatus of claim 4, wherein said at least one of said electrodes located proximate said distal end of said catheter is located within said drug delivery chamber.

6. The apparatus of claim 4, wherein said drug delivery chamber is expandable in a direction radial from a longitudinal axis of said catheter.

7. The apparatus of claim 6, wherein said drug delivery chamber is inflatable.

8. The apparatus of claim 4, wherein said permeable membrane further comprises a microporous membrane with pore sizes of less than 3 microns.

9. The apparatus of claim 4, wherein said permeable membrane further comprises a microporous membrane with pore sizes of less than 0.5 microns.

10. The apparatus of claim 4, wherein said drug delivery chamber further comprises at least one impermeable end section.

11. The apparatus of claim 4, wherein said permeable membrane is located around only a portion of a circumference of said catheter, wherein said drug delivery is substantially restricted to a portion of said circumference.

12. The apparatus of claim 1, wherein said drug delivery means comprises a polymer matrix material containing said drug for delivery to said internal body tissue.

13. The apparatus of claim 12, wherein said at least one of said electrodes located proximate said distal end of said catheter is located within said polymer matrix material.

14. The apparatus of claim 12, wherein said polymer matrix material is coaxially aligned about at least a longitudinal axis of said catheter.

15. The apparatus of claim 12, further comprising expansion means for expanding said polymer matrix material in a direction substantially radial to a longitudinal axis of said catheter.

16. The apparatus of claim 15, wherein said expansion means comprises a wire basket.

17. The apparatus of claim 15, wherein said expansion means comprises a balloon.

18. The apparatus of claim 1, further comprising means for sensing intrinsic cardiac activity.

19. The apparatus of claim 1, wherein said drug delivery current/voltage means supplies a pulsed waveform to said electrodes with a frequency of at least about 200 Hz.

20. The apparatus of claim 1, wherein said waveform has a frequency of at least about 2 kHz.

21. The apparatus of claim 1, wherein all of the electrodes connected to the catheter are configured to have the same polarity.

22. The apparatus of claim 1, wherein at least two of the electrodes connected to the catheter are configured to have an opposite polarity.

* * * * *